(12) United States Patent
Lepage et al.

(10) Patent No.: US 10,561,404 B2
(45) Date of Patent: Feb. 18, 2020

(54) GAPLESS CALIBRATION METHOD FOR PHASED ARRAY ULTRASONIC INSPECTION

(71) Applicants: Benoit Lepage, L'Ancienne-Lorette (CA); Guillaume Painchaud-April, L'Ancienne-Lorette (CA); Christophe Imbert, St. Augustin de Desmaures (CA); Charles Grimard, Quebec (CA)

(72) Inventors: Benoit Lepage, L'Ancienne-Lorette (CA); Guillaume Painchaud-April, L'Ancienne-Lorette (CA); Christophe Imbert, St. Augustin de Desmaures (CA); Charles Grimard, Quebec (CA)

(73) Assignee: Olympus Scientific Solutions Americas Inc., Waltham, MA (US)

( * ) Notice: Subject to any disclaimer, the term of this patent is extended or adjusted under 35 U.S.C. 154(b) by 69 days.

(21) Appl. No.: 15/611,959

(22) Filed: Jun. 2, 2017

(65) Prior Publication Data

US 2018/0000460 A1 Jan. 4, 2018

Related U.S. Application Data

(60) Provisional application No. 62/357,414, filed on Jul. 1, 2016.

(51) Int. Cl.
*A61B 8/00* (2006.01)
*A61B 17/22* (2006.01)
(Continued)

(52) U.S. Cl.
CPC ............ *A61B 8/587* (2013.01); *A61B 8/4218* (2013.01); *A61B 17/22004* (2013.01);
(Continued)

(58) Field of Classification Search
CPC . A61B 17/22004; A61B 8/4218; A61B 8/587; G01F 1/12; G01M 1/00; G01S 15/89; G01S 15/8913; G01S 7/5205
See application file for complete search history.

(56) References Cited

U.S. PATENT DOCUMENTS 3,646,805 A * 3/1972 Walters ................. G01N 29/38
 73/611
4,679,437 A * 7/1987 Koike .................... G01N 29/11
 73/622

(Continued)

*Primary Examiner* — Francis C Gray
(74) *Attorney, Agent, or Firm* — Gerald P. Kazanjian

(57) ABSTRACT

Disclosed is a calibration system and method for a phased array ultrasound pipe inspection system, in which reliable calibration is obtained for notches at all angles using only a small number of notches for the calibration. The method comprises a one-time normalization step and a system calibration step which may be performed at regular intervals. Ultrasound transmission is in a single diverging beam for each aperture, while reception is selective for multiple well-defined reception angles. During the normalization step, plots of maximum response vs reception angle are plotted for each notch, and a normalization curve is constructed by fitting the maxima of these plots. The normalization curve is used to derive calibration targets at specific reception angles for specific calibration notches, which are then used for the system calibrations.

32 Claims, 15 Drawing Sheets

(51) Int. Cl.
*G01F 1/12* (2006.01)
*G01S 7/52* (2006.01)
*G01S 15/89* (2006.01)
*G01M 1/00* (2006.01)

(52) U.S. Cl.
CPC ............ *G01F 1/12* (2013.01); *G01M 1/00* (2013.01); *G01S 7/5205* (2013.01); *G01S 15/89* (2013.01); *G01S 15/8913* (2013.01)

(56) References Cited

U.S. PATENT DOCUMENTS

| | | | | |
|---|---|---|---|---|
| 5,511,425 | A * | 4/1996 | Kleinert | G01N 29/069 73/609 |
| 8,115,919 | B2 * | 2/2012 | Yun | G01J 3/4412 356/301 |
| 2008/0111077 | A1 * | 5/2008 | Miller | G01N 21/39 250/339.07 |
| 2009/0146658 | A1 * | 6/2009 | McDowell | G01N 24/088 324/309 |
| 2010/0242613 | A1 * | 9/2010 | Simard | G01N 29/262 73/641 |
| 2011/0283798 | A1 * | 11/2011 | Yamano | G01N 29/043 73/632 |
| 2017/0284972 | A1 * | 10/2017 | Lepage | G01N 29/043 |

* cited by examiner

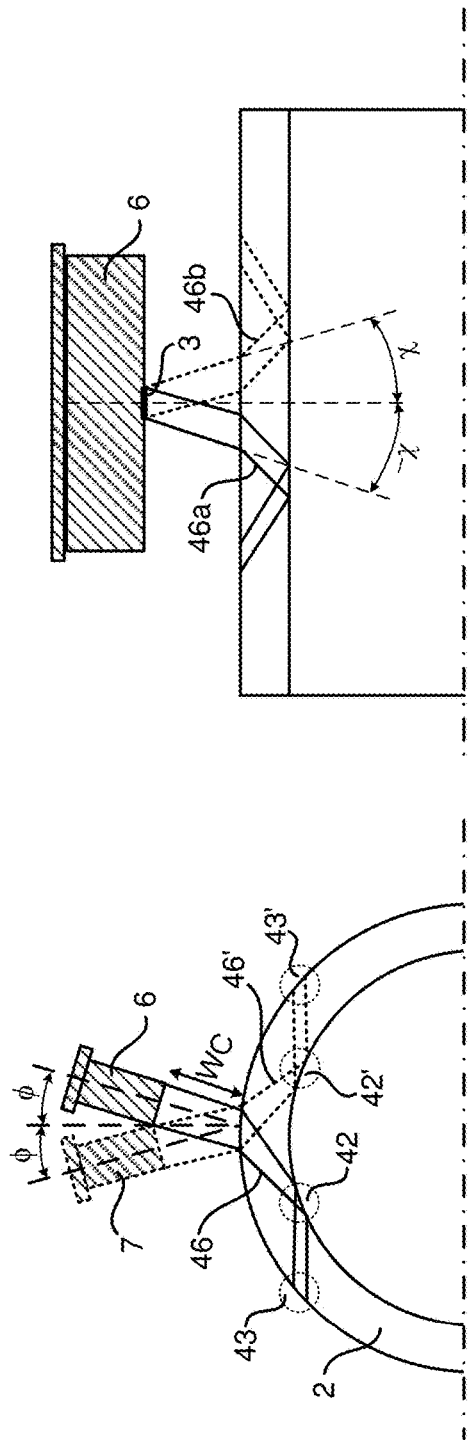
FIG. 4A
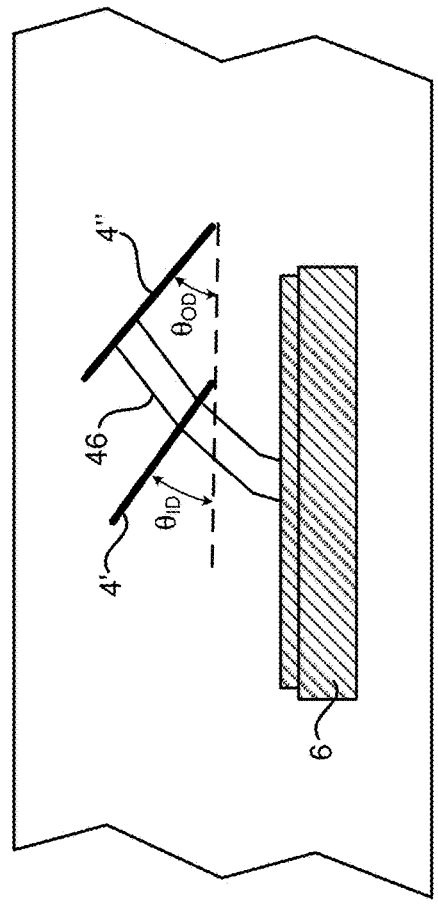
FIG. 4B
FIG. 4C

GAPLESS CALIBRATION METHOD FOR PHASED ARRAY ULTRASONIC INSPECTION

CROSS-REFERENCE TO RELATED APPLICATIONS

This application claims the benefit and priority of U.S. provisional patent application Ser. No. 62/357,414 filed Jul. 1, 2016 entitled GAPLESS CALIBRATION FOR RELIABLE INSPECTION OVER WIDE ANGULAR RANGE, the entire disclosure of which is incorporated herein by reference.

FIELD OF THE INVENTION

The invention relates to phased array ultrasound (PAUT) inspection of metal tubes, and more particularly to improved methods of calibrating echo response signals from defects so that substantially equivalent defects will produce the same response signal intensity irrespective of their angular orientation.

BACKGROUND OF THE INVENTION

Flaws required to be detected during PAUT inspection of tubes are often in the form of elongated defects having an angle θ with respect to the tube axis. Response from such defects is usually calibrated using a calibration tube which has a series of well-defined notches scribed on the outside diameter (OD) and inside diameter (ID) of the tube. The echo response amplitude from such notches is strongly peaked in the direction perpendicular to the length of the notch.

In existing practice, the echo response amplitude is calibrated for each notch on the calibration tube by receiving the scattered ultrasound energy in a direction perpendicular to the length of the notch. In this way, satisfactory calibration is achieved for actual angles of the calibration notches, but a calibration notch is required for every notch angle. Reliable calibration cannot be obtained for intermediate notch angles because of the non-linearity of the system. Thus the calibrations in existing practice exhibit "gaps" in the reliability of calibration with respect to notch angle.

In existing practice, the effect of the angular calibration gaps has been minimized by having a large number of calibration notches at closely spaced angular increments. However, such a method suffers disadvantages in the expense of machining the large number of notches required, and in the loss of productivity due to the time taken to perform calibrations on many notches.

Another disadvantage of calibrations in existing practice is that they rely on a single notch for calibration. It is known that multiple notches machined according to the same specification exhibit some variation with respect to detection amplitude. Accordingly, existing methods are very susceptible to these variations since the calibration depends entirely on a single notch.

Therefore there exists a need for a "gapless" calibration method which uses a small number of calibration notches with a reliable method of interpolating between calibration notch angles, and in which amplitude variations from a single notch are appropriately averaged. In view of their reliance on intermediate notches and on unreliable measurements from a single notch, existing methods are not able to provide gapless calibration.

SUMMARY OF THE INVENTION

Accordingly, it is a general objective of the present disclosure to provide a calibration method for phased array ultrasound (PAUT) inspection, wherein echo response signals from defects are calibrated so that substantially equivalent defects produce substantially the same response signal intensity irrespective of their angular orientation.

It is further an objective of the present disclosure to provide a gapless calibration method which uses a minimum number of calibration notches and provides a reliable method of interpolating between calibration notch angles.

It is further an objective of the present disclosure to provide echo response amplitudes having minimum variations over a reference level for defects of a defined size over a continuous range of angles and positions on the tube, and using a minimum number of calibration notches.

The objectives of the present invention may be achieved by performing a one-time acoustic normalization of the inspection system using a calibration tube with a small number of notches, located on both the tube ID and OD, and having different notch angles with respect to the tube axis. In an embodiment, the notches with non-zero notch angles are in pairs having equal and opposite notch angle. An angle response curve is plotted for each notch by measuring the peak response amplitude for a plurality of different reception angles.

In a first embodiment, angle response curves for each notch are measured with a single phased array (PA) probe, the measurement being repeated with the calibration tube first in normal and then in reversed orientation.

In a second embodiment, angle response curves for each notch are measured separately with two different PA probes having equal and opposite mechanical angles with respect to the surface normal of the calibration tube.

In a third embodiment, a single two-dimensional matrix PA probe is used and equal and opposite beam angles with respect to the surface normal of the calibration tube may be achieved by electronic steering of the ultrasonic beam.

A normalization curve is generated by constructing an envelope of the average peak values of the angle response curves for each notch angle. In an embodiment, the normalization curve is constructed by fitting a Lorentzian curve to each angle response curve and constructing the envelope of the modeled curves.

Having constructed a normalization curve with a one-time acoustic normalization procedure, the normalization curve is used to set calibration targets for subsequent periodic system calibrations performed periodically to verify the notch calibrations.

BRIEF DESCRIPTION OF THE DRAWINGS

FIG. 4A is a side view of a calibration apparatus according to the present disclosure.

FIG. 4B is a front view of a calibration apparatus according to the present disclosure.

FIG. 4C is a top view of a calibration apparatus according to the present disclosure.

DETAILED DESCRIPTION OF PREFERRED EMBODIMENT

In the description below, a one-time normalization procedure is referred to as "normalization" or "acoustic normalization". System calibration which occurs periodically (typically every 8 hours) during normal system operation is referred to as "calibration" or "system calibration". It should be noted that the use of a one-time normalization procedure is a novel and important aspect of the present disclosure.

In the description below, the term "notch" or "notches" is used to designate a notch or set of notches used during the normalization procedure. The term "calibration notch" or "calibration notches" is used to designate a notch or sub-set of notches used during system calibration.

In addition, in the description below, the terms "notch" or "notches" are used interchangeably with the terms "flaw" or "flaws". It is a known practice to those skilled in the art that "flaws" are often referred to as "notches" or "indications".

Figure 1:
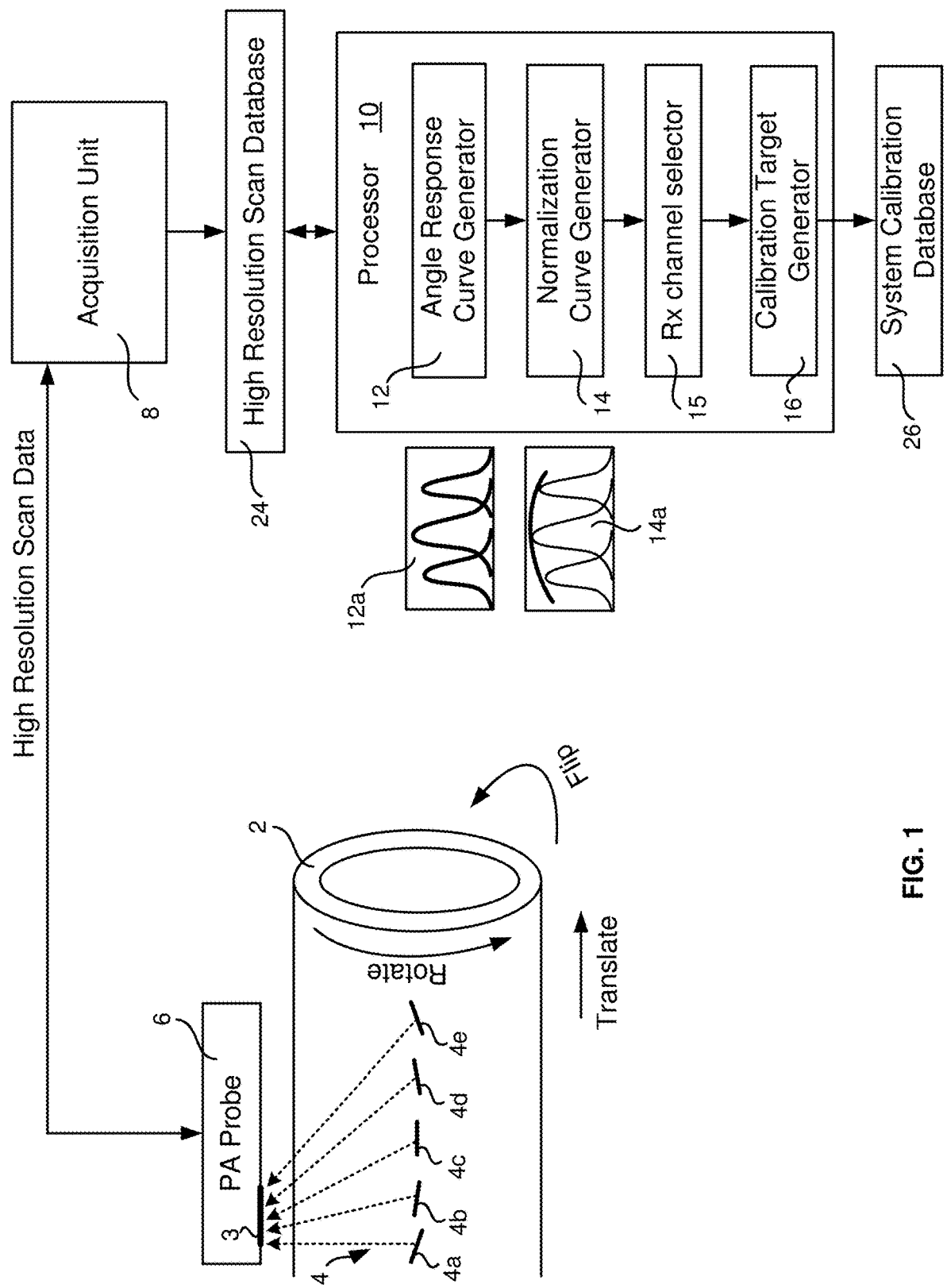
FIG. 1 is a schematic representation of a first embodiment of a calibration system according to the present disclosure.

In the description below, the following symbols are used:
Tx—transmitted beam
Rx—received beam
ID, OD—inside, outside diameter
$\theta$—notch angle relative to tube axis
$\chi$—Rx reception angle
$\phi$—probe mechanical angle
$c_1, c_2, c_3, c_4$—Lorentzian fitting parameters FIG. 1 shows an acoustic normalization system making use of a calibration tube 2, having a plurality of scribed notches 4a~4e. Note that FIG. 1 shows 5 notches, but any number of notches may be employed and all are within the scope of the invention. Note also that notches 4a~4e are representative of notches scribed on the ID and/or the OD of calibration tube 2. Notches 4a~4e have different notch angles $\theta$ with respect to the tube axis. In an embodiment, the notches with non-zero notch angles are in pairs having equal and opposite notch angle.

A PA probe 6 is ultrasonically coupled to calibration tube 2, usually by means of a water column (not shown). During the normalization procedure, calibration tube 2 may be rotated about its axis, translated in an axial direction or flipped between normal and reverse orientation as indicated by arrows in FIG. 1. The normalization procedure includes a high resolution scan which involves scanning the calibration tube 2 with high resolution, both with respect to spatial resolution of the rotation and translation, and also with respect to angular resolution of the reception angles. The purpose of the high resolution scan is to capture the maximum possible signal amplitude for each notch 4a~4e. During the scan, an active aperture 3 of PA probe 6 transmits ultrasound energy and receives echo signals 4 from notches 4a~4e, while calibration tube 2 is in normal orientation and is being rotated and translated. In order to obtain better statistics in measuring echoes from notches 4a~4e, the procedure is then repeated with calibration tube 2 in reverse orientation. Note that when the tube is in reverse orientation, echo signals are received from the opposite sides of each of notches 4a~4e, compared to when the tube is in normal orientation.

High resolution scan data is passed from PA probe 6 to an acquisition unit 8, and the data is stored in a high resolution scan database 24 which is in communication with a processor 10. Processor 10 includes an angle response curve generator 12, a normalization curve generator 14, an Rx channel selector 15 and a calibration target generator 16. Angle response curve generator 12 generates angle response curves, which are plots of the maximum echo response amplitude from each of notches 4a~4e as a function of reception angle of aperture 3. A graph 12a illustrates exemplary angle response curves from 3 notches. As will be further described below, there may be up to 4 different angle response curves for each of notches 4a~4e. The exemplary angle response curves of graph 12a may be taken to represent one set of angle response curves.

Normalization curve generator 14 generates a normalization curve which is an interpolation of the envelope of the angle response curves from notches 4a~4e. A graph 14a illustrates an exemplary normalization curve generated from the angle response curves shown in graph 12a.

Rx channel selector 15 selects an optimum set of reception channel angles to be used in subsequent system calibrations. Calibration target generator 16 uses the normalization curve to generate a calibration target in % full-scale height (% FSH) for each of the selected Rx channels when receiving from a specific calibration notch. The set of Rx channels and the % FSH calibration targets together comprise a system calibration database 26, which is the output of the acoustic normalization system and is used for all subsequent system calibrations.

Figure 2:
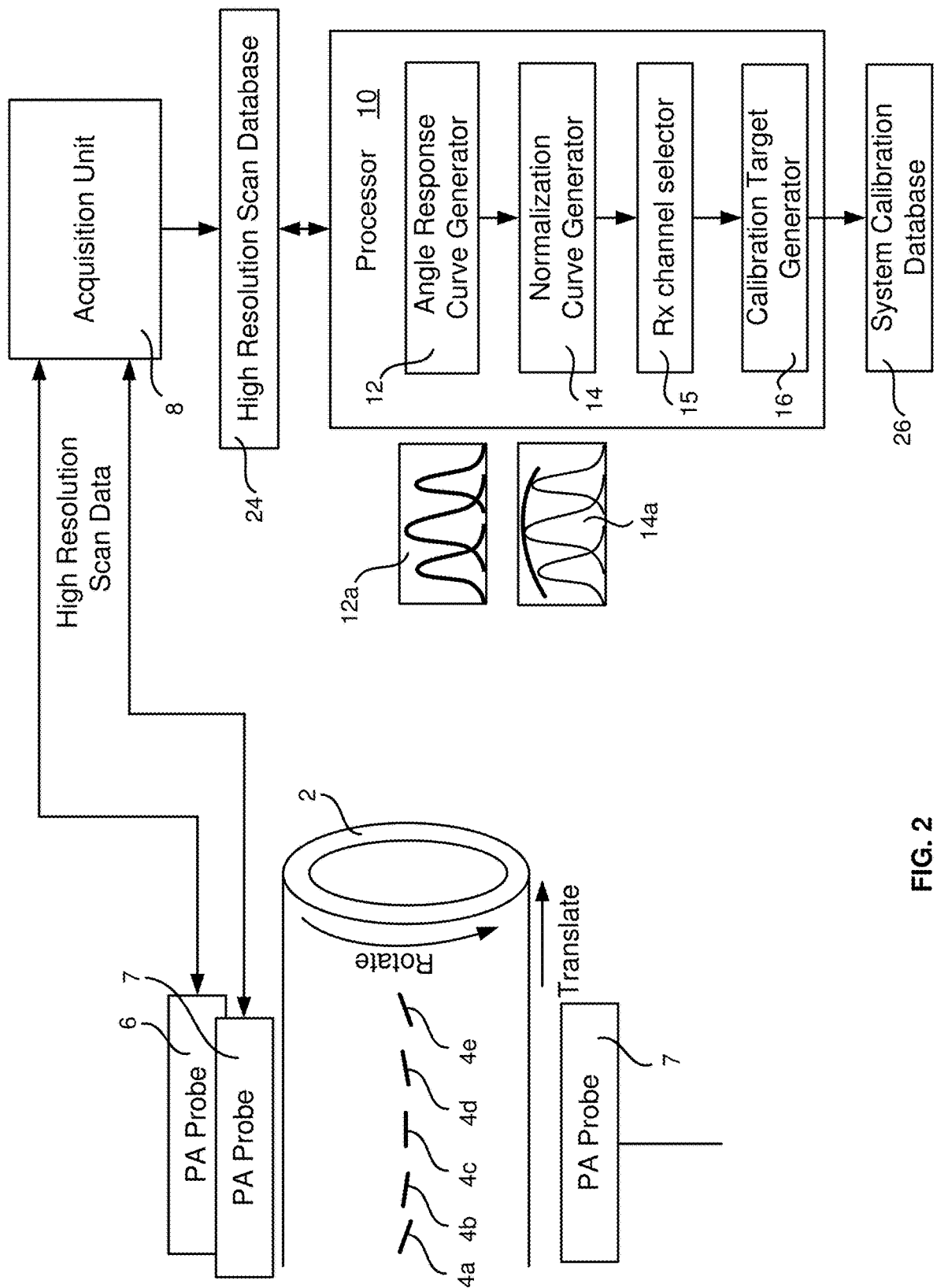
FIG. 2 is a schematic representation of a second embodiment of a calibration system according to the present disclosure.

FIG. 2 illustrates an alternative embodiment of an acoustic normalization system. A second PA probe 7 is located such that probes 6 and 7 have equal and opposite mechanical angles with respect to the surface normal of the calibration tube (see FIG. 4A), and acquisition unit 8 receives high resolution scan data from both PA probe 6 and PA probe 7. Flipping the tube between normal and reverse orientation as in FIG. 1, is not required in the embodiment of FIG. 2 since the function of obtaining better measurement statistics is replaced by second PA probe 7. Note also that PA probe 6 and PA probe 7 receive echo signals from opposite sides of notches 4a~4e. Based on the assumption that the average notch response seen by both PA probe 6 and PA probe 7 should therefore be approximately equal, the sensitivities of PA probe 6 and PA probe 7 are equalized by averaging the total response from notches 4a~4e.

In a third embodiment of an acoustic normalization system, probe 6 is a two-dimensional matrix probe which has a first dimension in a plane perpendicular to the calibration tube axis and a second dimension parallel to the calibration tube axis. In the first dimension, the matrix probe receives data by electronic processing in two directions making equal and opposite angles with respect to the surface normal of the calibration tube. The second dimension of the matrix probe is for acquiring high resolution scan data for generating angle response curves, Thus, using a single matrix probe eliminates the requirement to flip the calibration tube.

Figure 3:
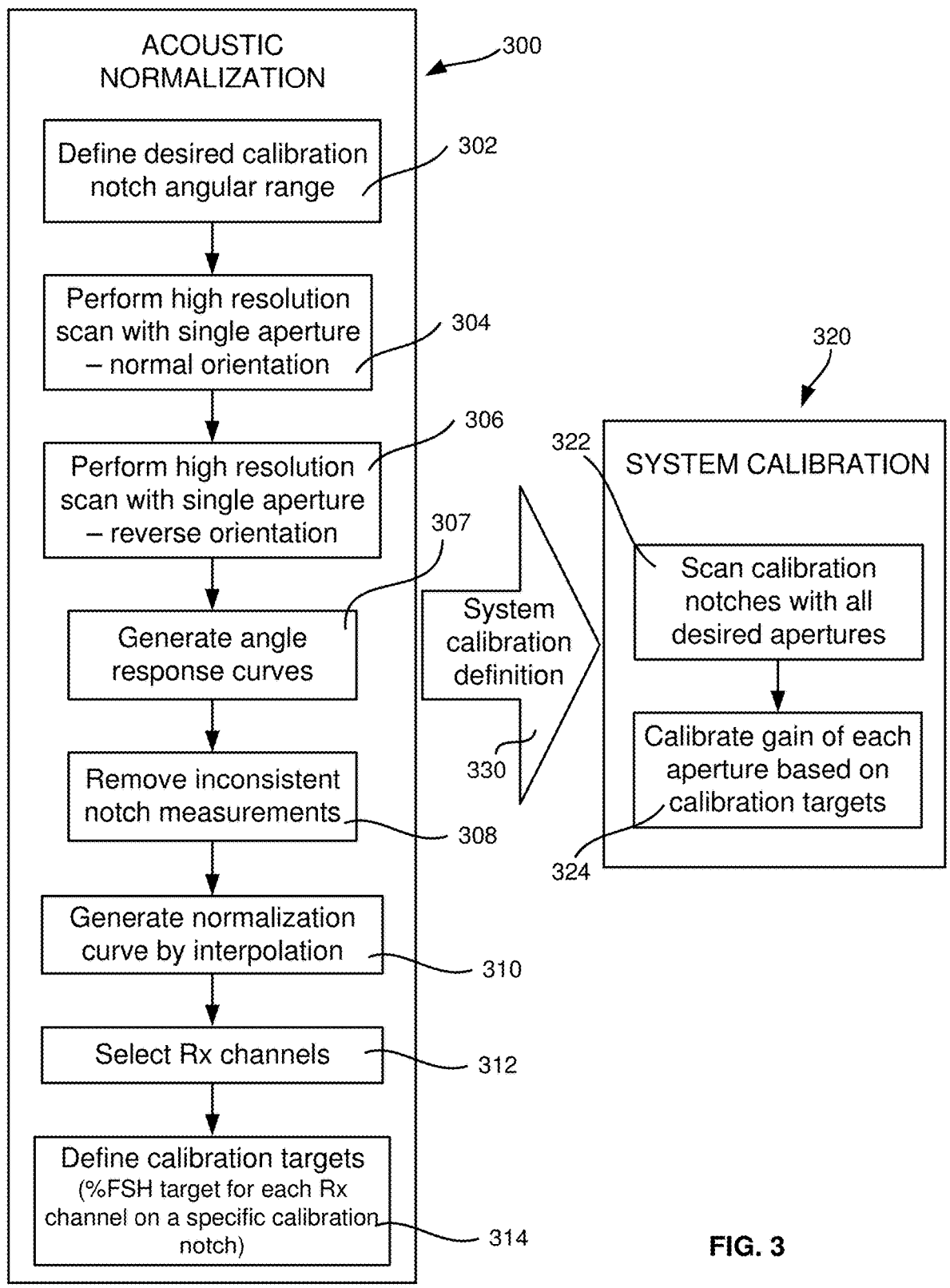
FIG. 3 is a flow chart of a calibration method according to the present disclosure.

FIG. 3 is a flow chart of a gapless calibration method according to the present disclosure. The method comprises an acoustic normalization step 300 and a system calibration step 320, wherein acoustic normalization step 300 is a one-time step and system calibration step 320 may be performed periodically, for example every 8 hours, during regular system operation. Acoustic normalization step 300 and system calibration step 320 are linked by a system calibration definition 330, which is a set of Rx channels and % FSH calibration targets generated by acoustic normalization step 300 for use by system calibration step 320.

In step 302 of acoustic normalization step 300, a desired notch angular range of the calibration is selected, either automatically or by operator input, and a calibration tube is selected containing at least 3 OD notches and/or at least 3 ID notches having notch angles substantially within the desired range. In step 304 a high resolution scan of the calibration tube is performed with the tube in normal orientation, using a single probe aperture with a broad transmitted beam and multiple reception angles. In step 306 a similar high resolution scan of the calibration tube is performed with the tube in reverse orientation. In alternative embodiments, methods other than the scanning methods of steps 304 and 306 may be used to gather response information from the notches, and all such methods are within the scope of the present invention. In step 307, C-Scan data from the high resolution scans is used to derive the maximum response amplitude from each notch, and thereby to generate angle response curves, which are plots of the maximum response amplitude as a function of the aperture reception angle, $\chi$. Up to four angle response curves may be generated for each notch, corresponding respectively to normal tube orientation, positive notch angle (hereinafter normal+), reversed tube orientation, positive notch angle (reversed+), normal tube orientation, negative notch angle (normal−), reversed tube orientation, negative notch angle (reversed−).

In an optional step 308, any inconsistent notch measurements may be removed from the set of angle response curves. An inconsistent notch measurement may be, for example, one of four angle response curves from the same notch, wherein one of the curves differs greatly from the other three. Such inconsistencies may be due to imperfections in the machining of the notches, or to thickness changes of the pipe on the different signal paths of the four angle response curves. By optionally eliminating notch data with such inconsistencies, the acoustic normalization may avoid being biased by the quality of individual notches.

In step 310 a normalization curve is generated from the angle response curves from different notches. The normalization curve may be generated by extrapolating between the maximum values of the most probable response curve at each notch angle, where the maximum value of the most probable response curve for each notch angle may be taken to be the average of the maximum values of the angle response curves for each notch. In an alternative embodiment, the normalization curve may be generated by fitting a Lorentzian curve to each angle response curve and constructing the envelope of the modeled curves.

In step 312 a set of Rx channels is selected for use in system calibration 320. In step 314 % FSH calibration targets are defined for each of the selected Rx channels, each calibration target being linked to a specific one of a defined set of calibration notches. The linked notches for use in system calibration 320 are hereinafter referred to as "calibration notches". An alternative embodiment is to use a flaw that is not a notch for calibration (for example a through drilled hole). In this case, it is necessary to include the desired calibration flaw in the high resolution scan of the normalization step. A flaw which is not a notch may not be used to generate the normalization curve because it is not representative of a real flaw having a given angle. However, such a flaw may still be used as a reference to calibrate the system because if it is included in the high resolution curve then its relationship relative to the normalization curve is known, and hence the gain may be set based on the flaw response. The advantage is that if the flaw is a hole, all laws may be calibrated on this single hole because the hole reflects at all angles.

In step 322 of system calibration 320 the calibration notches are scanned using all the desired apertures of PA probe 6. Note that the scan of calibration notches is performed only at the Rx channels selected at step 312, meaning that the scan of step 322 is performed at lower resolution with respect to Rx angle than the normalization scans of step 304 or 306. In step 324 the gain of each of the desired apertures is calibrated based on the % FSH calibration targets for each selected Rx channel and the corresponding linked calibration notches.

Note that in existing practice it is necessary to have transmission and reception angles which provide optimal specular reflection from each calibration notch in order to obtain maximum signal response. This complicates the selection of calibration notches and limits the choice of reception angles. In contrast, the present invention allows reliable calibration using a selection of Rx channels and linked calibration notches where the reception angle is not required to provide optimal specular reflection from the calibration notch and the signal response is not required to be maximum for the linked calibration notch.

FIGS. 4A, 4B and 4C illustrate a PAUT inspection system for gapless flaw detection according to the present invention. FIG. 4A is a side view of the system, showing a PA probe 7 for clockwise (CW) inspection and a PA probe 6 for counter-clockwise (CCW) inspection. It is therefore not necessary to flip tube 2 with the inspection system shown in FIGS. 4A, 4B and 4C. Probes 6 and 7 are tilted at mechanical angles ±ϕ to the surface normal of tube 2 and are each acoustically coupled to tube 2 by a water column of length WC. Each active aperture of probe 6 or probe 7 generates a single wide defocused transmitted beam, and multiple received beams with high angular selectivity are used in post-processing to discriminate and process the information from a range of notch angles.

Figure 5A:
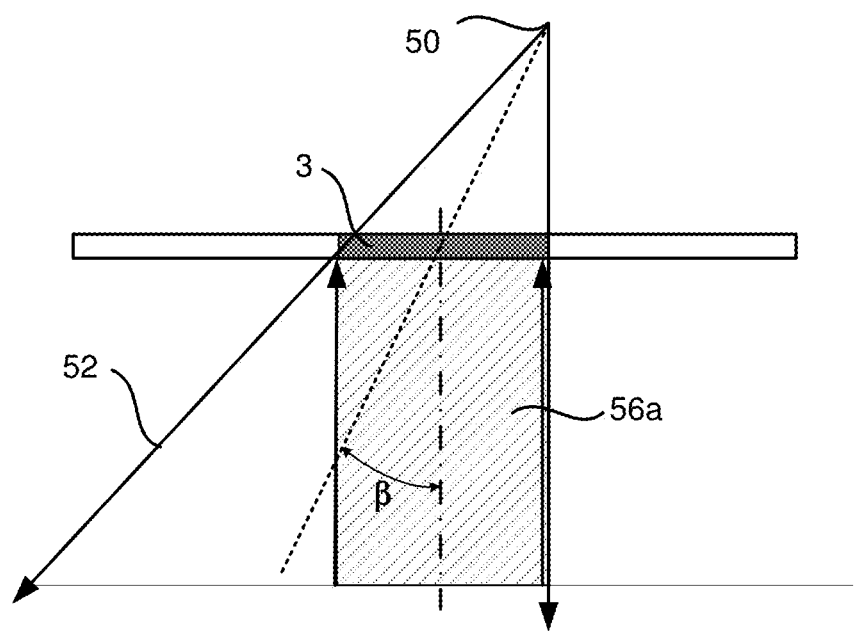
FIG. 5A is a schematic illustrations of a beam transmission with reception at zero degrees according to the present disclosure.
Figure 5B:
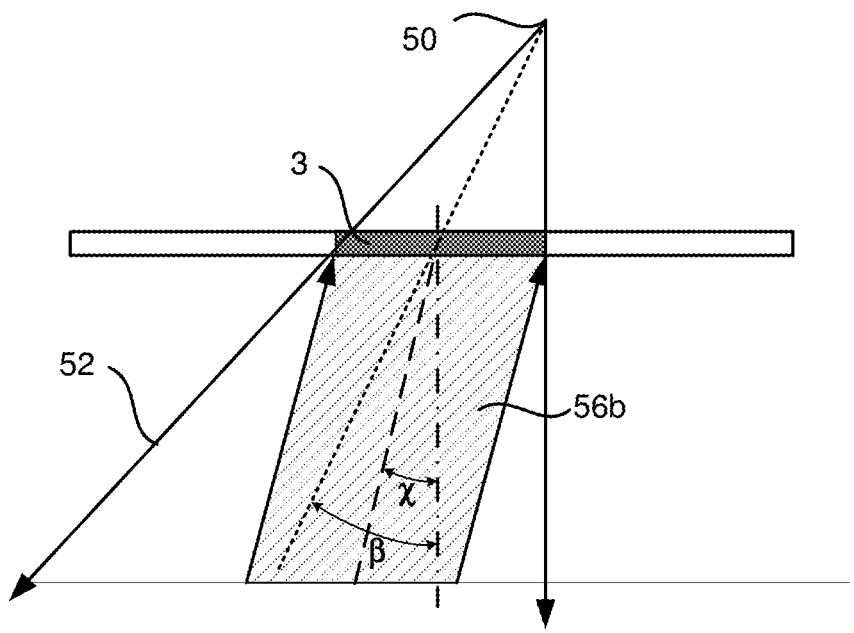
FIG. 5B is a schematic illustrations of a beam transmission with reception at angle $\chi$ according to the present disclosure.

FIGS. 5A and 5B further illustrate the method of single transmission and multiple reception. In FIG. 5A a diverging transmitted beam 52 is emitted from an aperture 3 of PA probe 6, with a focal point 50 located behind aperture 3. The mid-angle ray of transmitted beam 52 forms an angle β; with the normal to aperture 3. A received beam 56a normal to aperture 3 is used in post-processing. In FIG. 5B, aperture 3 emits the same transmitted beam 52, but a received beam 56b used in post-processing has an angle χ relative to the normal to aperture 3. Thus a given transmission (Tx) definition provides detection capability over an angle range χ through the use of multiple receptions (Rx). In operation of the PAUT inspection system, the whole surface of PA probes 6 or 7 is covered by generating the Tx definition from a plurality of different aperture positions on the probe. Multiple apertures having the same Tx definition are referred to as a "Tx Group".

Returning now to FIG. 4A, exemplary Rx beams 46 and 46' are shown being received by PA probes 6 and 7 respectively. Rx beam 46 includes indications from ID flaws located in an ID region 42, and indications from OD flaws located in an OD region 43. Rx beam 46' includes indications from ID flaws located in an ID region 42', and indications from OD flaws located in an OD region 43'.

FIG. 4B is a front view of the inspection system, showing aperture 3 and exemplary Rx beams 46a and 46b having Rx angles −χ and χ respectively. Note that by means of different Rx laws in post-processing, the Rx angle χ may be varied over a wide range.

FIG. 4C is a top view of the inspection system, showing an exemplary ID notch 4' located in ID region 42 and an exemplary OD notch 4" located in OD region 43. Notches 4' and 4" have angles $\theta_{ID}$ and $\theta_{OD}$ with respect to the axis of tube 2. Notches 4' and 4" are detected by Rx beam 46, but note that Rx beam 46 at Rx angle χ is not necessarily perpendicular to the long direction of either notch 4' or notch 4". It is an important aspect of the present invention that, as described below, the gain of aperture 3 may be calibrated even though Rx beam 46 is not perpendicular to either notch 4' or notch 4".

It is an objective of the present invention to provide calibrated detection of any notch having an angle θ between −45 and +45 degrees. In an embodiment of the invention the following clusters of probes, probe mechanical angles and Tx groups may be used to achieve the objective:

Cluster#1:
φ=17 degrees for −22 to 22 degree notch angles.
Probe 7 oriented for clockwise (CW) inspection.
A first Tx Group with positive Rx angle χ for −22 to 0 degree notches.
A second Tx Group with negative Rx angle χ for 0 to 22 degree notches Cluster#2:
φ=17 degrees for −22 to 22 degree notch angles.
Probe 6 oriented for counter-clockwise (CCW) inspection.
A first Tx Group with positive Rx angle χ for −22 to 0 degree notches.
A second Tx Group with negative Rx angle χ for 0 to 22 degree notches Cluster#3:
φ=14 degrees for 122 to 451 degree notch angles.
Probe 7 oriented for clockwise (CW) inspection.
A first Tx Group with positive Rx angle χ for −22 to −45 degree notches.
A second Tx Group with negative Rx angle χ for 22 to 45 degree notches Cluster#4:
φ=14 degrees for 122 to 451 degree notch angles.
Probe 6 oriented for counter-clockwise (CCW) inspection.
A first Tx Group with positive Rx angle χ for −22 to −45 degree notches.
A second Tx Group with negative Rx angle χ for 22 to 45 degree notches Note that these clusters are presented by way of example only. They are sufficient to achieve the objectives of the present invention, but other cluster combinations may be used to achieve the same or different objectives, and all such combinations are within the scope of the present invention.

Figure 6:
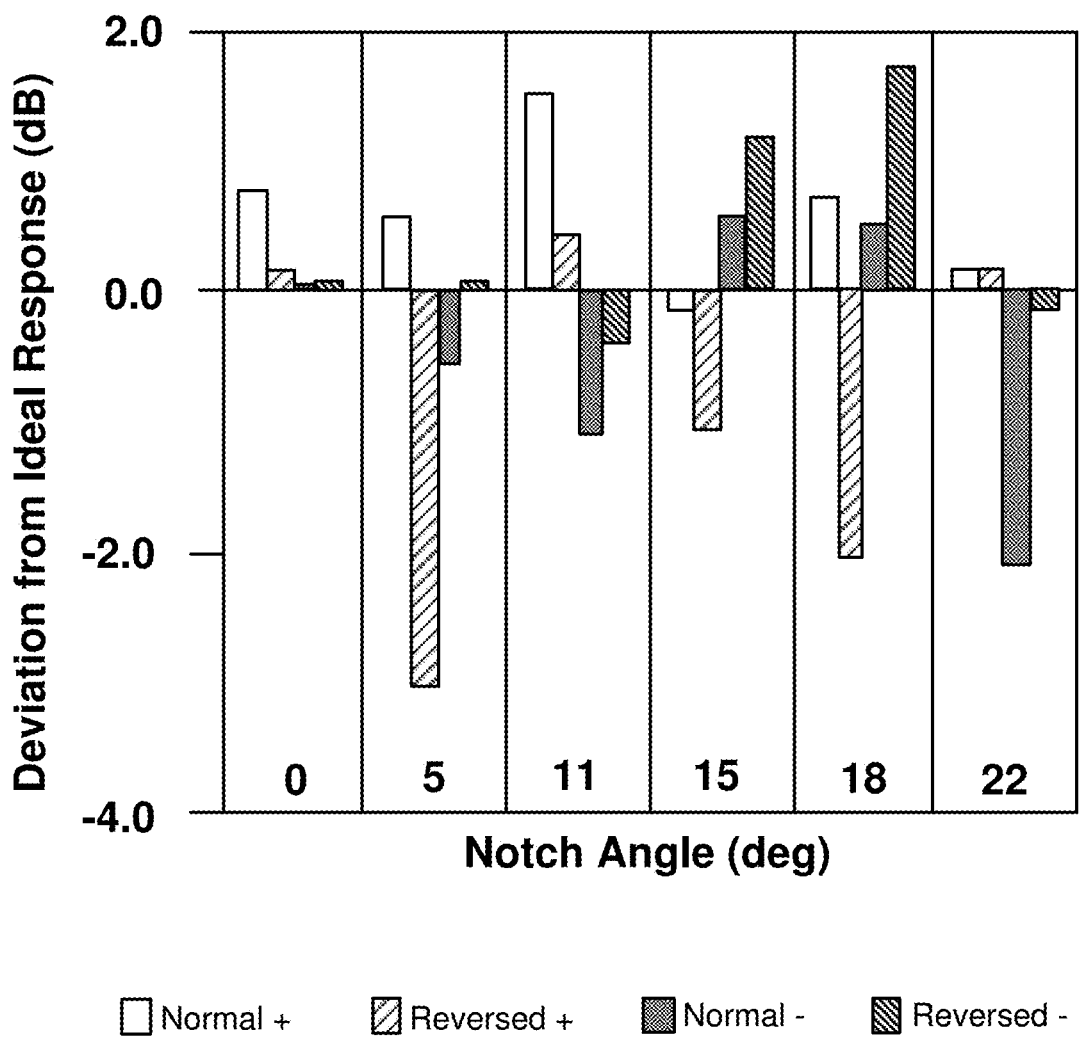
FIG. 6 is a graph of response deviation from various OD notches.

It is an objective of the present invention to perform extrapolations to cover the angular gap between existing calibration notches. However, since the calibration notches are not perfect, the extrapolation method should avoid being biased by poor quality of any individual notch. As an example, FIG. 6 shows the measured response from OD notches machined with high precision on a reference tube. The notches have angles with respect to the tube axis of 0°, ±5°, ±11°, ±15°, ±18°, ±22°, and each notch pair was measured with the tube in both normal and reversed orientation. The data is plotted relative to the anticipated response on a "perfect" tube with "perfect" notches, for which the responses for positive or negative notch angle and normal or reversed tube orientation should all be equal. FIG. 6 shows that real notches exhibit large deviations from the ideal case, and it can be easily understood that if a bad notch is selected for the calibration (for example, 5° reversed+), then there may be serious inaccuracies in the calibration. Such deviations from the ideal may be caused by varying notch quality or by any non-uniformity (such as wall thickness variations or varying pipe curvature) which lies on the acoustic path. It should be noted that data such as that shown in FIG. 6 may be used to eliminate inconsistent notch measurements from the calibration data set, in accordance with step 308 of FIG. 3. For example, the data corresponding to 5° reversed+ may be removed from the interpolation data. Removal of inconsistent data may be implemented by optional addition of a consistency checking unit (not shown) to the calibration systems illustrated in FIGS. 1 and 2.

Figure 7:
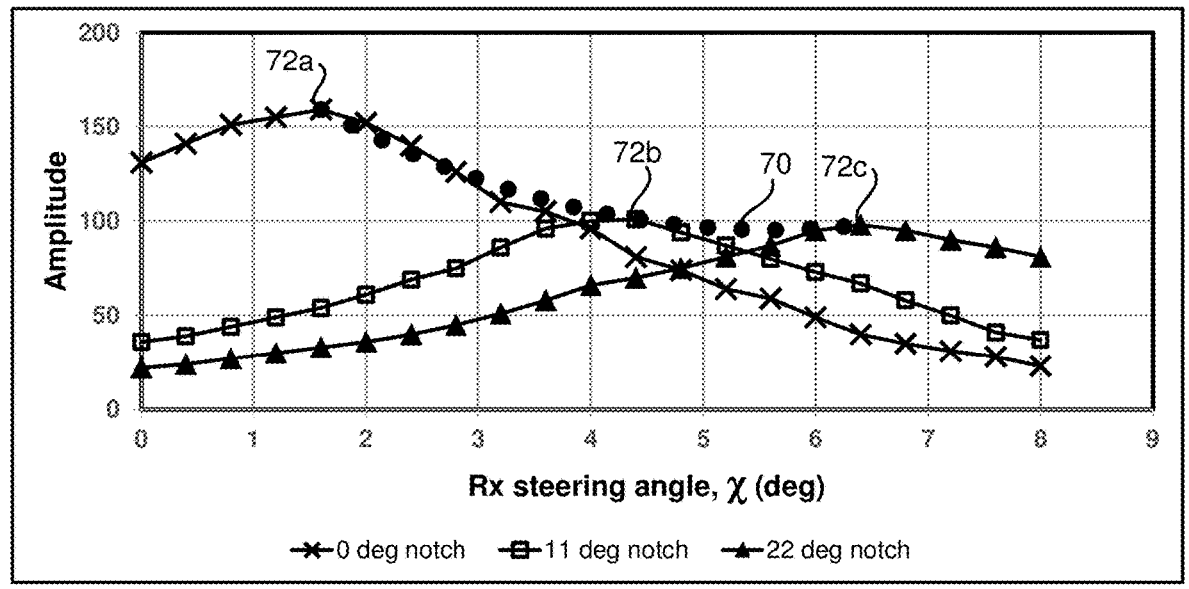
FIG. 7 shows Rx angle response curves for three OD notches.
Figure 8:
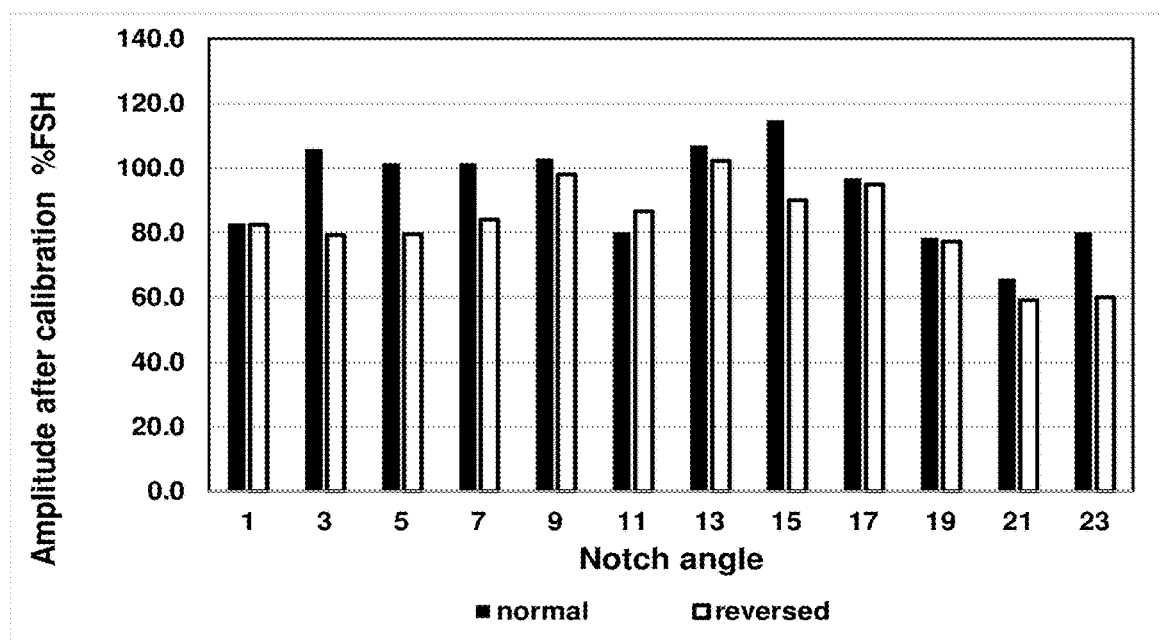
FIG. 8 is a graph of amplitude after calibration for a large set of notches.

In view of the deviations of notch responses, calibration inaccuracies may also occur if there is insufficient statistical data for the calibration. FIG. 7 shows angle response curves for a 177 mm×10 mm calibration tube measured only in normal orientation for only three notches having notch angles of 0°, +11° and +22°, and with the Tx beam oriented towards the 0 to +22 degree notch range. The angle response curves have maximum values 72a, 72b and 72c respectively, and a normalization curve 70 is constructed by interpolation between the maximum values. Calibration gain parameters based on normalization curve 70 were then applied to the system so as to bring the normalization curve to a constant response amplitude of 80% FSH. Using these calibration gain parameters, a large set of notches having notch angles from +1° to +23° in increments of 2° was then scanned, with the tube in both normal and reversed orientations. FIG. 8 shows the resulting amplitude after calibration for each notch. It is seen that there is unacceptably large variation (up to 5.8 dB) from the desired amplitude of 80% FSH for all notches. The conclusion is that calibration with only one angle response curve from only 3 notches was not successful.

Figure 9:
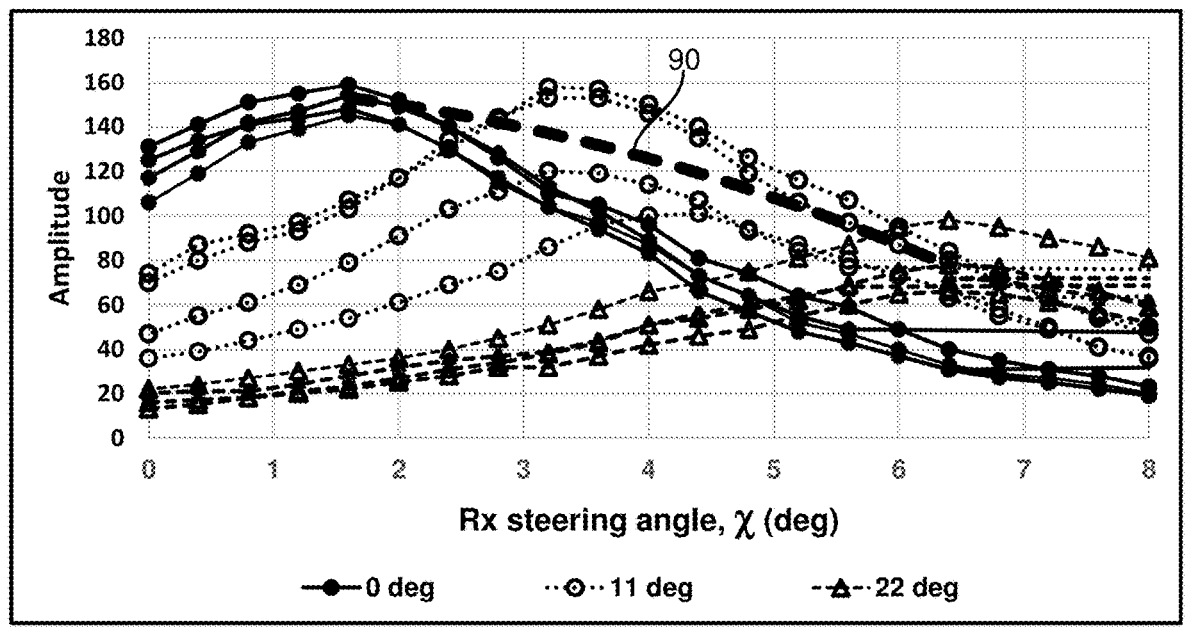
FIG. 9 shows Rx angle response curves for three OD notches, including tube reversal and notch symmetry.

FIG. 9 shows the result of adding more statistics to the calibration data. This was achieved by including scans over each notch in both normal and reverse tube orientation, and by considering the system to be symmetrical (i.e. assuming that normalization curves are the same for notches with positive and negative notch angles of the same magnitude). FIG. 9 therefore shows four angle response curves for each notch angle, namely normal+, reversed+, normal− and reversed−. A normalization curve 90 is constructed by interpolation between the average maximum values (not shown) of the four angle response curves for each notch angle.

Figure 10:
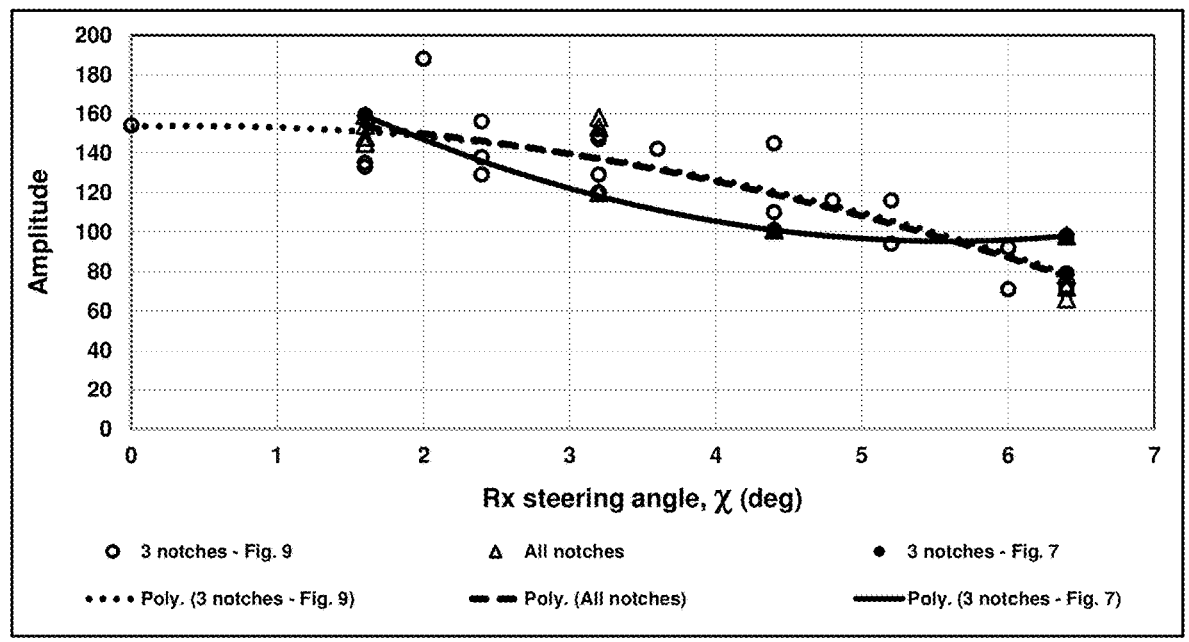
FIG. 10 is a graph showing comparison of normalization curves.

FIG. 10 compares the normalization curves obtained with three different methods. The curve labeled "3 notches—FIG. 7" and its polynomial fit correspond to normalization curve 70 in FIG. 7 obtained with only normal tube orientation and no symmetry assumption. The curve labelled "3 notches—FIG. 9" and its polynomial fit correspond to normalization curve 90 in FIG. 9 obtained with both normal and reversed tube orientation and including both positive and negative notch angles. The curve labelled "all notches" corresponds to measurements using a large set of notches having notch angles from +1° to +23° in increments of 2°, and therefore this curve is the most accurate representation of the correct normalization curve. It can be seen that the polynomial fit for "3 notches—FIG. 9" corresponds closely to the polynomial fit for "all notches", whereas the polynomial fit for "3 notches—FIG. 7" deviates substantially. Therefore, the use of additional data obtained by reversal of the tube orientation and using symmetrically opposite notch angles allows a normalization curve derived from only 3 notches to closely correspond to normalization curve derived from a large number (12 or more) notches. It should be noted that this is a novel and important aspect of the present disclosure.

The normalization curves of the previous figures were derived by interpolation between maxima or average maxima of angle response curves using a simple polynomial fitting procedure. The description below in connection with FIGS. 11~15 is an outline of an optional extension of the fitting methods which includes a fitting model for each angle response curve, and derivation of an envelope for the normalization curve.

Figure 11A:
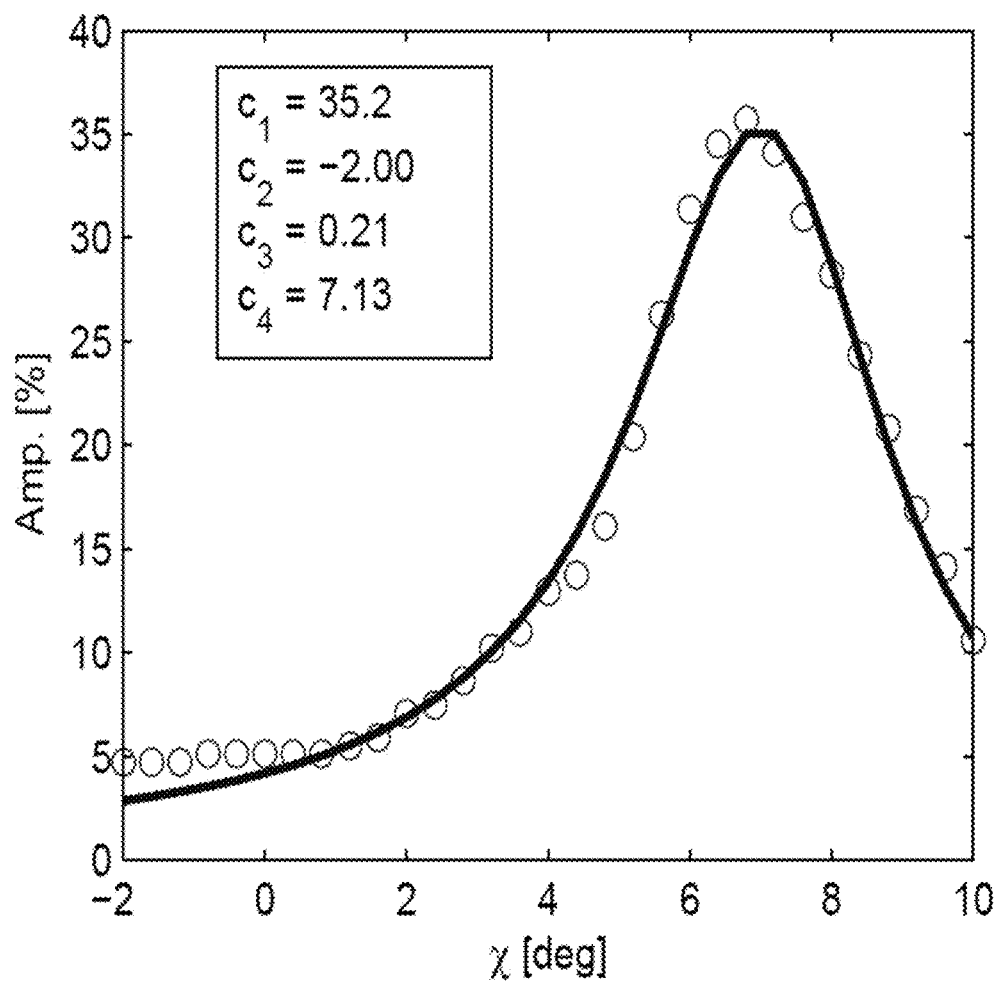
FIG. 11A shows a Lorentzian function fit to the data points of an Rx angle response curve.

FIG. 11A shows a fit to an empirical angle response curve using a Lorentzian function of the form $$L(\gamma) = \frac{c_1 + c_2(\gamma - c_4)}{1 + c_3(\gamma - c_4)^2} \quad (1)$$

where
$c_1$ is the maximum amplitude value over the Rx angle $\chi$ range (un-skewed case)
$c_2$ is the skewness parameter
$c_3$ is the width parameter
$c_4$ is the value of Rx angle $\chi$ at the position of the maximum.
The values of the $c_n$ parameters used for the fit are shown in the inset of FIG. 11A. It has been found that such a Lorentzian function is able to provide a good fit for all angle response curves within the range of applicability of the present invention.

Figure 11B:
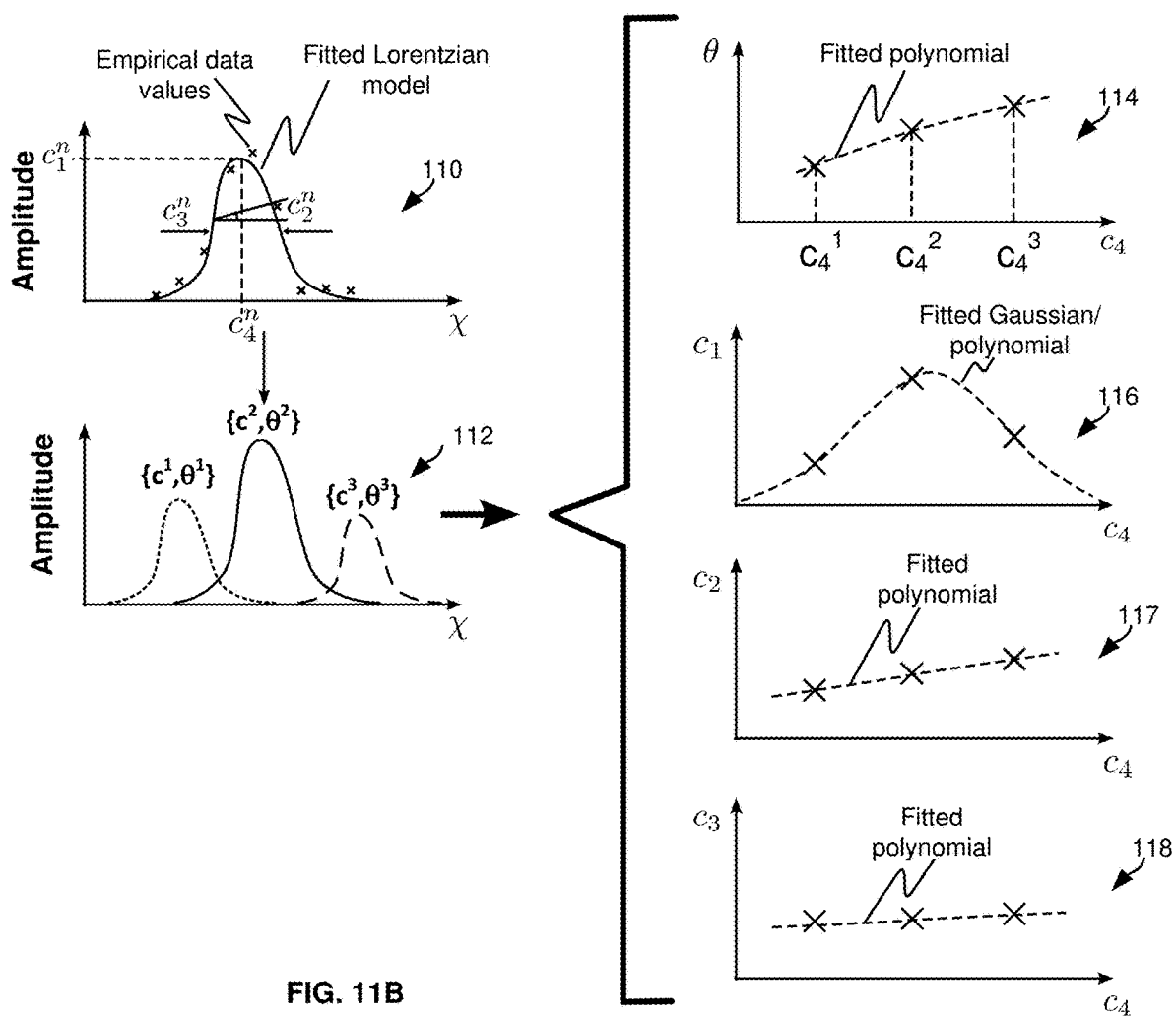
FIG. 11B is an illustration of a method of fitting Lorentzian function parameters to a series of Rx angle response curves.

FIG. 11B illustrates a method by which Lorentzian fits for angle response curves corresponding to three notch angles may be used to generate a complete set of Lorentzian curves which may be associated with any notch angle within the applicable range. In FIG. 11B, a graph 110 illustrates the Lorentzian fit for an angle response curve for the $n^{th}$ notch, wherein the Lorentzian fit parameters are $c_1^n$, $c_2^n$, $c_3^n$, and $c_4^n$. A graph 112 illustrates Lorentzian fits for three notches having notch angles $\theta^1$, $\theta^2$, and $\theta^3$ and c parameters $c_i^1$, $c_i^2$ and $c_i^3$, with i=1, 2, 3 and 4. In graph 114, $c_4^1$, $c_4^2$ and $c_4^3$ are plotted against $\theta^1$, $\theta^2$, and $\theta^3$, and the three points on the graph are fitted with a polynomial. In graph 116, $c_4^1$, $c_4^2$ and $c_4^3$ are plotted against $c_1^1$, $c_1^2$ and $c_1^3$, and the three points on the graph are fitted with a Gaussian or a polynomial. In graph 117, $c_4^1$, $c_4^2$ and $c_4^3$ are plotted against $c_2^1$, $c_2^2$ and $c_2^3$, and the three points on the graph are fitted with a Gaussian or a polynomial. In graph 118, $c_4^1$, $c_4^2$ and $c_4^3$ are plotted against $c_3^1$, $c_3^2$ and $c_3^3$, and the three points on the graph are fitted with a Gaussian or a polynomial.

Figure 12:
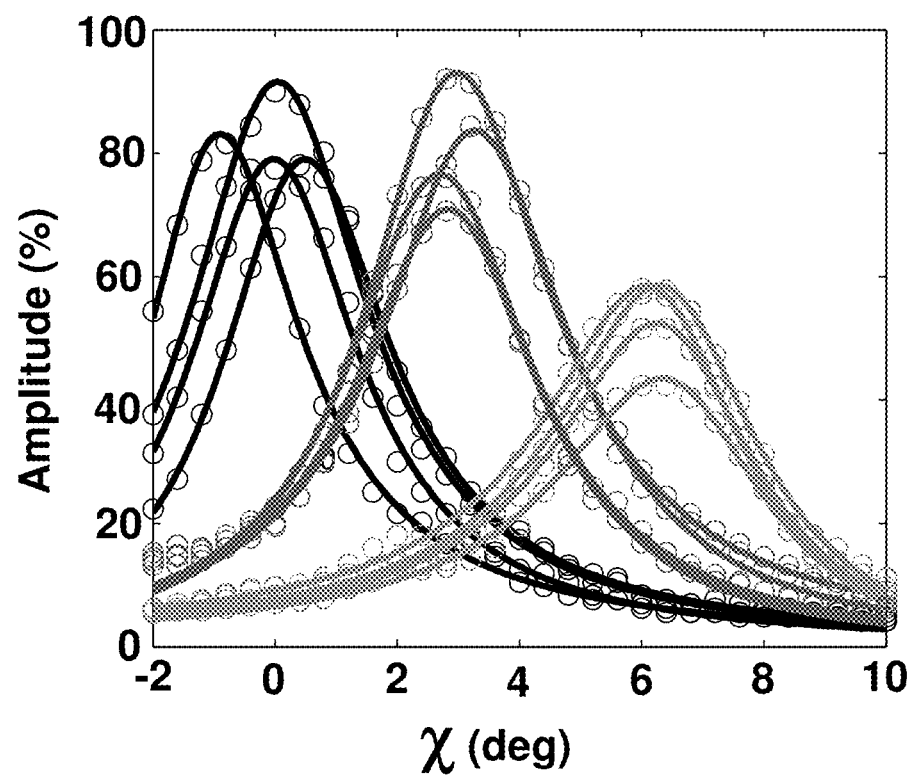
FIG. 12 shows Lorentzian function fits to Rx angle response curves for three OD notches, including tube reversal and notch symmetry.
Figure 13A:
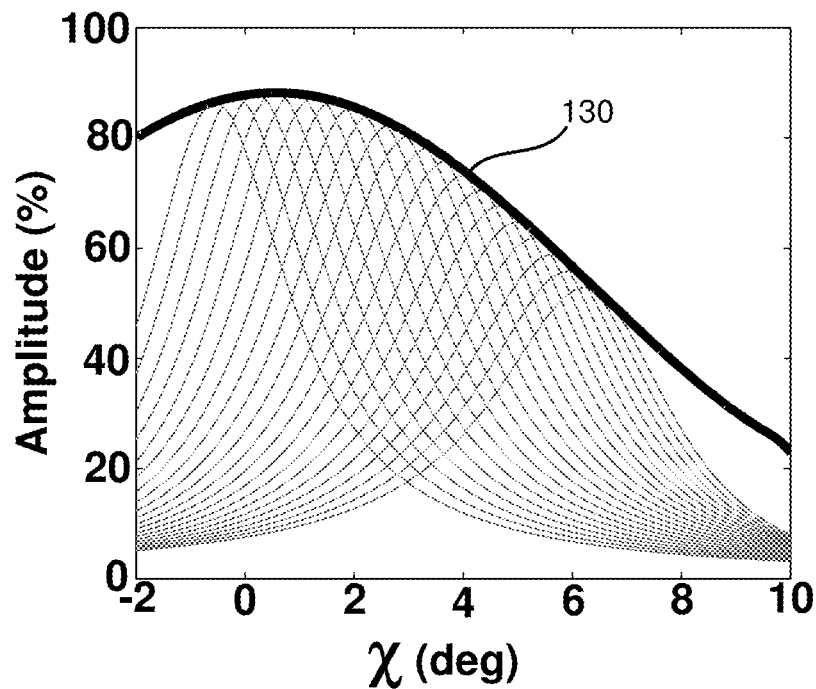
FIG. 13A shows the envelope of a set of most probable Lorentzian function fits for a closely spaced series of notch angles.

The regression process of FIG. 11B is repeated for all angle response curves (including reverse orientation and negative Tx alignment) and for each of the three notches. FIG. 12 shows an example of the result of this regression process for 3 notches each having 4 angle response curves. With this data, the most probable parameter values of the Lorentzian function may be determined over the complete range of notch angles $\theta$ and the envelope of the most probable values may be determined. FIG. 13A shows the most probable Lorentzian functions based on the reference data set of FIG. 9. The many curves presented in FIG. 13A are plotted for a closely spaced series of values of notch angle $\theta$, ($\theta=0°$ to 22° in steps of 1°), and are the most probable ones according to the evolution of estimated Lorentzian c parameters over the range of interest of notch angles $\theta$. A curve 130 forms the envelope of the stacked Lorentzian curves, and corresponds to the normalization curve for the system. In principle, curve 130 represents the maximum detectable signal from any notch angle $\theta$, and it is therefore a good calibration reference.

Figure 13B:
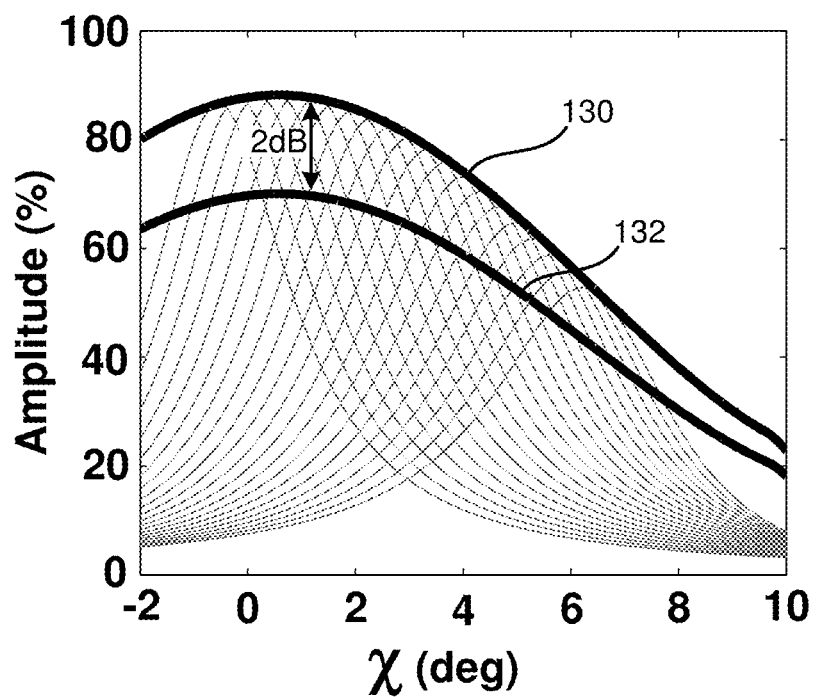
FIG. 13B illustrates a 2 dB homogeneity target derived from the most probable envelope.

Once envelope curve 130 has been determined from the multiple data regressions, it is possible to look for an appropriate selection of Rx angles to use for the inspection. It should be understood that because of device and productivity limitations high density sampling of Rx angle is not feasible. A desired number of Rx angles to be used for the inspection is specified by the user, and the optimum values of these angles are determined by means of a user-defined response homogeneity target for all notches within the range. FIG. 13B illustrates a response homogeneity target 132 which is 2 dB below the normalization curve 130. The meaning of response homogeneity target 132 is that all notches within the $\theta$ range of interest should have an expected detection amplitude between curve 130, which is the most probable maximum response, and homogeneity target 132. Note that the value of 2 dB in FIG. 13B represents a possible user selection for the homogeneity target, but any choice is possible and all are within the scope of the present invention.

Selection of Rx channels is accomplished by constructing the Lorentzian angle response curves $L(\chi,\theta_{min})$ and $L(\chi,\theta_{max})$ as determined by equation (1) for the minimum and maximum values $\theta_{min}$ and $\theta_{max}$ of the desired notch angle range. The curves $L(\chi,\theta_{min})$ and $L(\chi,\theta_{max})$ are overlaid on FIG. 13B (not shown) and minimum and maximum Rx angles, $\chi_{min}$ and $\chi_{max}$, are selected so as to obtain an expected response amplitude which is between normalization curve 130 and homogeneity target 132. Having selected $\chi_{min}$ and $\chi_{max}$, the remaining Rx channels may be selected by specifying values of $\chi$ which are equally spaced between $\chi_{min}$ and $\chi_{max}$.

Figure 14A:
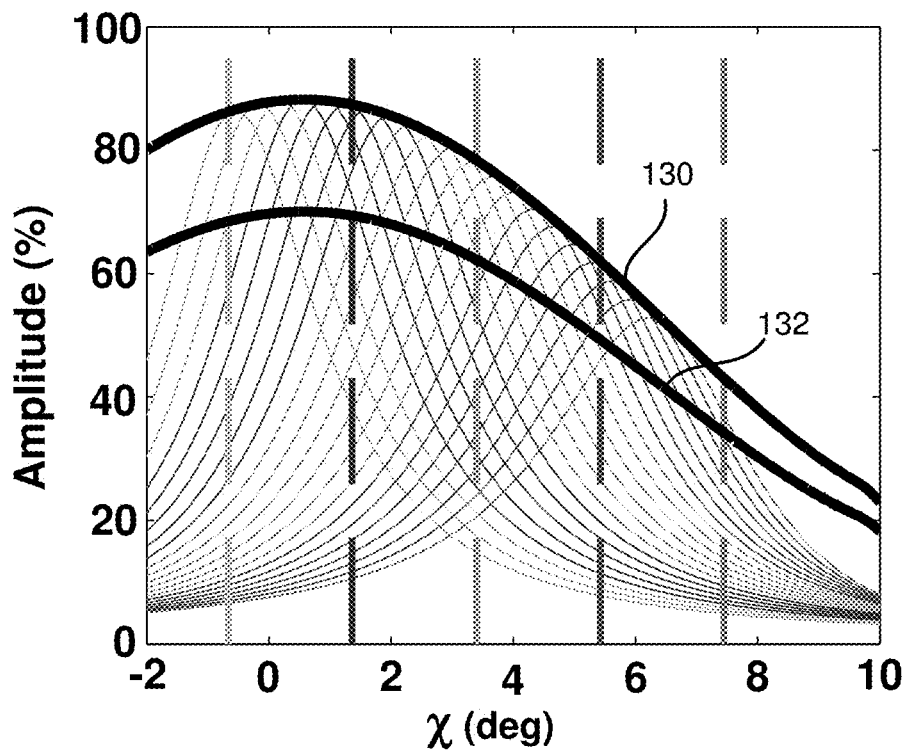
FIG. 14A shows fitted Rx angle response curves and selected Rx channels for the calibration.
Figure 14B:
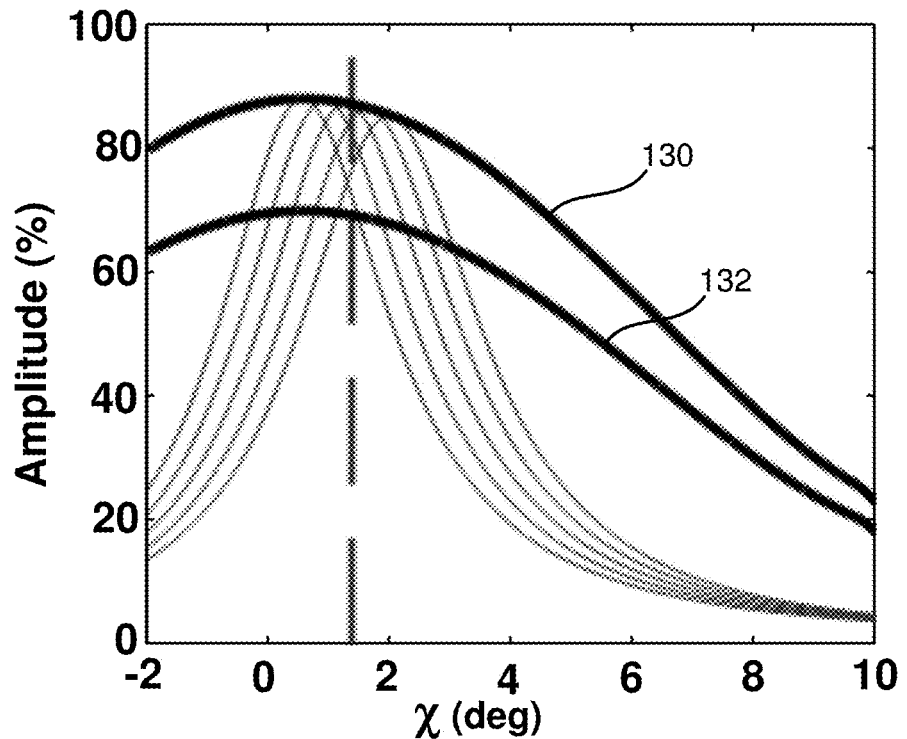
FIG. 14B shows the association between a sub-set of fitted Rx angle response curves and an Rx channel at 1.5°.

FIG. 14A is an illustration of the most probable Rx angle response curves for OD notches with angles $\theta$ within the range of interest, and showing five selected Rx channels (vertical dashed lines) at Rx angles of −0.5, 1.5, 3.5, 5.5 and 7.5 degrees. In the figure, each Rx channel is associated with a number of angle response curves based on the capacity of a given channel to detect a given notch with amplitude above homogeneity target 132. A specific example of the association is illustrated in FIG. 14B, in which only angle response curves associated with Rx angle of 1.5 degrees are shown. It is seen that the associated angle response curves all have values between normalization curve 130 and homogeneity target 132 at the associated Rx angle $\chi$=1.5 degrees.

Figure 15:
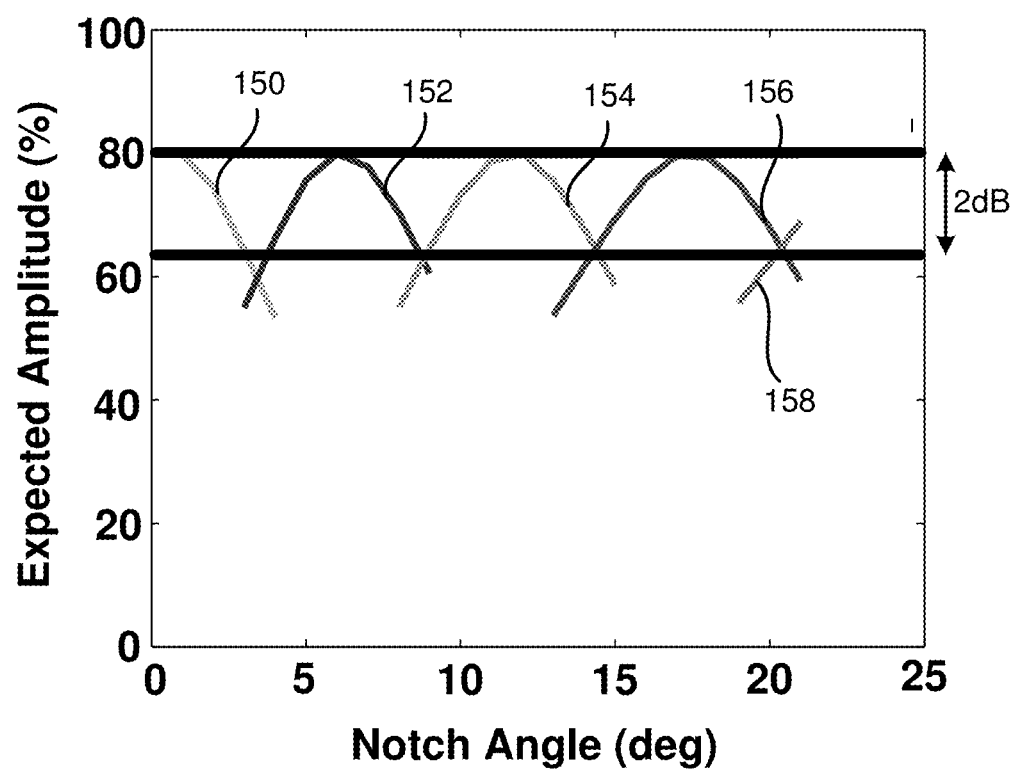
FIG. 15 is a graph of the expected response amplitude as a function of the notch angle.

From the associated angle response curves of FIGS. 14A and 14B, the expected response as a function of notch angle may be determined for each of the selected Rx channels. In FIG. 15, curves 150, 152, 154, 156 and 158 show the expected response amplitude as a function of notch angle for Rx angles of −0.5, 1.5, 3.5, 5.5 and 7.5 degrees respectively. The amplitude has been calibrated to have a maximum response of 80% at each Rx channel. With one exception at about 4 degrees, the response for any notch angle within the range from 0 to 22 degrees is always greater than 63%, corresponding to an amplitude reduction of 2 dB, as specified by homogeneity target 132.

Once the Rx channels have been selected, calibration targets for any selected calibration notch may be derived. For an Rx channel at $\chi=\chi_m$, the gain factor needed to achieve an amplitude of 80% FSH for the maximum notch response is given by $$g(\chi_m) = 80/C(\chi_m) \quad (2)$$

where $C(\chi_m)$ is the value of normalization curve 130 at the $\chi_m$ reception angle. However, the maximum response for the selected notch will likely not occur at reception angle $\chi_m$. The expected response amplitude $r(\chi_m)$ is given by the value of the most probable angle response curve of the selected notch at $\chi=\chi_m$. The calibration target for the selected notch at reception angle $\chi_m$ is therefore given by:

$$\text{calibration target} = g(\chi_m) r(\chi_m) \quad (3)$$

or $$\text{calibration target} = 80(\chi_m)/C(\chi_m) \quad (4)$$

Note that since there are four angle response curves corresponding to normal+, reversed+, normal− and reversed− orientations, normalization step 300 (see FIG. 3) will in general produce four different calibration targets for each selected calibration notch and for each Rx angle. The calibration targets are included in system calibration definition 330. System calibration step 320 will then use only the calibration targets which are appropriate for the system orientation being used for the system calibration.

Figure 16:
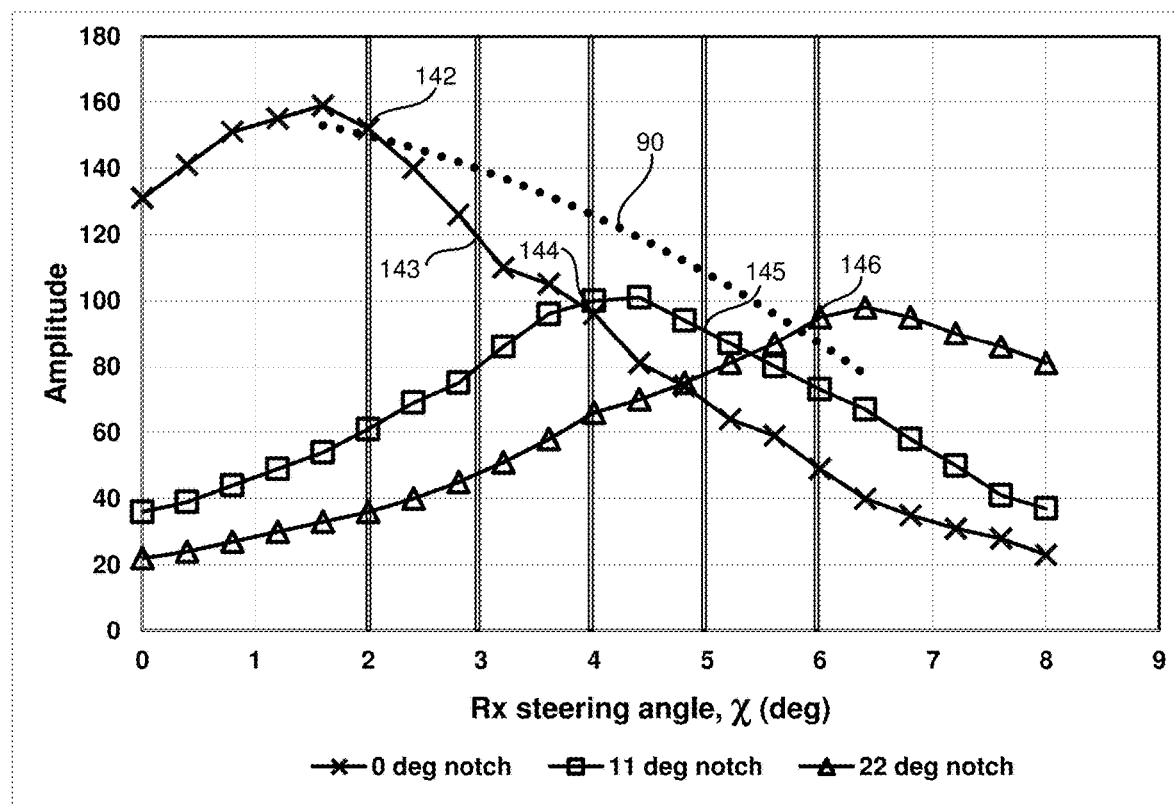
FIG. 16 shows Rx channel selections and calibration targets derived from the data of FIG. 9.

Note also that the Lorentzian fitting procedure described herein is optional, and any suitable fitting procedure may be used. For example, FIG. 16 shows calibrations and Rx channel selections derived from the data in FIG. 9. Normalization curve 90 is derived by interpolation between average maximum values of the Rx angle response curves of FIG. 9. In FIG. 16 only the normal+Rx angle response curve for each notch is displayed, since this is the orientation to be used for calibration. For this normalization the selected Rx channels are $\chi_m$=2, 3, 4, 5 and 6 degrees as shown by the vertical double lines in FIG. 16. By applying equation (4) with $C(\chi)$ corresponding to normalization curve 90, it can be shown that the appropriate calibration targets are 78% FSH target at Rx=2° on 0° notch (intersection point 142), 68% FSH target at Rx=3° on 0° notch (intersection point 143), 64% FSH target at Rx=4° on 11° notch (intersection point 144), 65% FSH target at Rx=5° on 11° notch (intersection point 145) and 87% FSH target at Rx=6° on 22° notch (intersection point 146).

Although the present invention has been described in relation to particular embodiments thereof, it can be appreciated that various designs can be conceived based on the teachings of the present disclosure, and all are within the scope of the present disclosure.

What is claimed is:

1. A phased array ultrasound inspection system comprising a calibration system, the calibration system comprising:
a calibration object having an axis with an axial direction, the calibration object having a plurality of flaws, each flaw having a long direction making a flaw angle with respect to the axial direction;
at least one phased array probe having a probe surface sonically coupled to the calibration object, wherein each one of the at least one phased array probe has at least one aperture emitting an ultrasonic beam and receiving a maximum echo response from each of the plurality of flaws at a series of reception angles with respect to a probe surface normal direction;
an acquisition unit configured to acquire scan data from the at least one probe;
a processor configured to generate a system calibration database, the processor comprising:
an angle response curve generator configured to generate angle response curves for each of the plurality of flaws, wherein the angle response curves are plots of the maximum echo response as a function of the reception angle;
a normalization curve generator configured to generate a normalization curve, wherein the normalization curve is a plot of a most probable maximum echo response value as a function of the reception angle;
a reception channel selector configured to select a plurality of reception channels, wherein each reception channel corresponds to a selected reception angle; and,
a calibration target generator configured to generate a plurality of calibration targets, wherein each calibration target is defined so as to bring the normalization curve to a predetermined level after calibration, wherein each calibration target is a target for the maximum echo response from one of a plurality of calibration flaws at a corresponding reception channel, and wherein the calibration flaws are selected ones of the plurality of flaws; and,
wherein the system calibration database comprises the plurality of reception channels and the calibration targets for the calibration flaws.

2. The inspection system of claim 1 wherein the calibration object is a calibration tube and wherein the plurality of flaws is machined on at least one of an inner surface of the calibration tube and an outer surface of the calibration tube.

3. The inspection system of claim 2 wherein the calibration tube is rotated about the axis and translated in the axial direction during acquisition of the scan data.

4. The inspection system of claim 3 wherein the scan data comprises data acquired with the calibration tube in a normal orientation and a reversed orientation, wherein the calibration tube is flipped so as to reverse the axial direction between the normal and the reversed orientations.

5. The inspection system of claim 3 wherein the at least one probe comprises two probes, the two probes being mounted so that the two probe surface normal directions make equal and opposite angles with respect to a calibration tube surface normal, and wherein the scan data acquired by the two probes is substantially equivalent to the scan data of a single probe acquisition wherein the calibration tube is flipped so as to reverse the axial direction during the single probe acquisition.

6. The inspection system of claim 3 wherein the at least one probe comprises a two-dimensional matrix probe having a first dimension in a plane perpendicular to the axial direction and a second dimension parallel to the axial direction, the matrix probe configured to receive data in two matrix reception directions in the first dimension, the two matrix reception directions making equal and opposite angles with respect to a surface normal of the calibration tube, and wherein the scan data acquired by the two-dimensional matrix probe in the second dimension is equivalent to the scan data of a single probe acquisition wherein the calibration tube is flipped so as to reverse the axial direction during the single probe acquisition.

7. The inspection system of claim 1 wherein the plurality of flaws comprises pairs of flaws, wherein the flaw angles of each pair are a positive flaw angle and a negative flaw angle, wherein the positive flaw angle is equal and opposite to the negative flaw angle, and wherein the angle response curve generator generates two angle response curves for each pair of flaws, the two angle response curves corresponding to the positive flaw angle and the negative flaw angle.

8. The inspection system of claim 4 wherein the plurality of flaws comprises pairs of flaws, wherein the flaw angles of each pair are a positive flaw angle and a negative flaw angle, wherein the positive flaw angle is equal and opposite to the negative flaw angle, and wherein the angle response curve generator generates four angle response curves for each pair of flaws, the four angle response curves corresponding to combinations of the normal orientation and the reversed orientation with the positive flaw angle and the negative flaw angle.

9. The inspection system of claim 7 wherein the most probable maximum echo response value is an average value of maxima of the two angle response curves for each pair of flaws.

10. The inspection system of claim 8 wherein the most probable maximum echo response value is an average value of the maxima of the four angle response curves for each pair of flaws.

11. The inspection system of claim 8 further comprising a consistency checking unit configured to check consistency of the four angle response curves and for removing inconsistent angle response curves, wherein the inconsistent angle response curves are one or more of the four angle response curves which deviate from a user defined consistency criterion.

12. The inspection system of claim 1 wherein the angle response curve generator employs a curve fitting function having fitting parameters to produce fitted curves for each one of the angle response curves, and parameter fitting functions to fit the dependence of each of the fitting parameters on flaw angle.

13. The inspection system of claim 12 wherein the angle response curve generator uses the parameter fitting functions to construct fitted angle response curves for a series of flaw fitting angles, wherein at least one of the flaw fitting angles does not correspond to a flaw angle.

14. The inspection system of claim 13 wherein the normalization curve corresponds to an envelope of maximum values of the fitted angle response curves.

15. The inspection system of claim 12 wherein the curve fitting function is a Lorentzian function.

16. A method of calibrating a phased array ultrasound inspection system, the method comprising a normalization step and a calibration step;
wherein the normalization step comprises:
performing a normalization scan to acquire normalization scan data with at least one phased array probe sonically coupled to a calibration object having an axis with an axial direction, the calibration object having a plurality of flaws, each flaw having a long direction making a flaw angle with respect to the axial direction, wherein each one of the at least one phased array probe has at least one aperture emitting an ultrasonic beam and receiving a maximum echo response from each of the plurality of flaws at a series of reception angles with respect to a probe surface normal direction;
generating angle response curves for each of the plurality of flaws, wherein the angle response curves are plots of the maximum echo response as a function of the reception angle;
generating a normalization curve, wherein the normalization curve is a plot of a most probable maximum echo response value as a function of the reception angle;
selecting a plurality of reception channels, wherein each reception channel corresponds to a selected reception angle;
generating a plurality of calibration targets, wherein each calibration target is defined so as to bring the normalization curve to a predetermined level after calibration, wherein each calibration target is a target for the maximum echo response from one of a plurality of calibration flaws at a corresponding reception channel, and wherein the calibration flaws are selected ones of the plurality of flaws; and,
wherein the calibration step comprises:
performing a calibration scan of the calibration flaws on the calibration object, wherein a plurality of apertures from each of the at least one phased array probe emits ultrasonic beams and receives the maximum echo responses from the calibration flaws at the corresponding reception channels; and
calibrating the gain of each of the plurality of apertures based on the calibration targets.

17. The method of claim 16 wherein the normalization step is performed one time for a system setup and the calibration step is performed multiple times at specified intervals to verify the calibration targets.

18. The inspection system of claim 16 wherein the calibration object is a calibration tube and wherein the plurality of flaws is machined on at least one of an inner surface of the calibration tube and an outer surface of the calibration tube.

19. The inspection system of claim 16 wherein the calibration tube is rotated about the axis and translated in the axial direction while performing the normalization scan.

20. The method of claim 19 wherein the normalization scan is performed with the calibration tube in a normal orientation and a reversed orientation, and wherein the calibration tube is flipped so as to reverse the axial direction between the normal and the reversed orientations.

21. The method of claim 19 wherein the at least one probe comprises two probes, the two probes being mounted so that the two probe surface normal directions make equal and opposite angles with respect to a calibration tube surface normal, and wherein the normalization scan data acquired by the two probes is equivalent to the normalization scan data of a single probe acquisition wherein the calibration tube is flipped so as to reverse the axial direction during the single probe acquisition.

22. The method of claim 19 wherein the at least one probe comprises a two-dimensional matrix probe having a first dimension in a plane perpendicular to the axial direction and a second dimension parallel to the axial direction, the matrix probe configured to receive data in two matrix reception directions in the first dimension, the two matrix reception directions making equal and opposite angles with respect to a surface normal of the calibration tube, and wherein the normalization scan data acquired by the two-dimensional matrix probe in the second dimension is equivalent to the normalization scan data of a single one-dimensional probe acquisition wherein the calibration tube is flipped so as to reverse the axial direction during the single probe acquisition.

23. The method of claim 16 wherein the plurality of flaws comprises pairs of flaws, wherein the flaw angles of each pair are a positive flaw angle and a negative flaw angle, wherein the positive flaw angle is equal and opposite to the negative flaw angle, and wherein the angle response curve generator generates two angle response curves for each pair of flaws, the two angle response curves corresponding to the positive flaw angle and the negative flaw angle.

24. The method of claim 20 wherein the plurality of flaws comprises pairs of flaws, wherein the flaw angles of each pair are a positive flaw angle and a negative flaw angle, wherein the positive flaw angle is equal and opposite to the negative flaw angle, and wherein the angle response curve generator generates four angle response curves for each pair of flaws, the four angle response curves corresponding to combinations of the normal orientation and the reversed orientation with the positive flaw angle and the negative flaw angle.

25. The method of claim 23 wherein the most probable maximum echo response value is an average value of maxima of the two angle response curves for each pair of flaws.

26. The method of claim 24 wherein the most probable maximum echo response value is an average value of maxima of the four angle response curves for each pair of flaws.

27. The method of claim 24 further comprising a consistency checking step for checking consistency of the four angle response curves and for removing inconsistent angle response curves, wherein the inconsistent angle response curves are one or more of the four angle response curves which deviate from a user defined consistency criterion.

28. The method of claim 16 wherein the step of generating angle response curves further comprises employing a curve fitting function having fitting parameters to produce fitted curves for each one of the angle response curves, and parameter fitting functions to fit the dependence of each of the fitting parameters on flaw angle.

29. The method of claim 28 wherein the step of generating angle response curves further comprises using the parameter fitting functions to construct fitted angle response curves for a series of flaw fitting angles, wherein at least one of the flaw fitting angles does not correspond to a flaw angle.

30. The method of claim 29 wherein the normalization curve corresponds to an envelope of maximum values of the fitted angle response curves.

31. The method of claim 28 wherein the curve fitting function is a Lorentzian function.

32. The method of claim 16 wherein the normalization scan has a higher resolution with respect to the reception angles than the calibration scan.

\* \* \* \* \*